US005498263A

United States Patent [19]
DiNello et al.

[11] Patent Number: 5,498,263
[45] Date of Patent: Mar. 12, 1996

[54] TRANSVERSE CONNECTOR FOR SPINAL COLUMN CORRECTIVE DEVICES

[75] Inventors: Alexandre M. DiNello, Skaker Heights; Bryan D. Hildebrand, Cleveland Heights; Hoyt D. White, Mentor, all of Ohio

[73] Assignee: AcroMed Corporation, Cleveland, Ohio

[21] Appl. No.: 267,871

[22] Filed: Jun. 28, 1994

[51] Int. Cl.$^6$ .......................... A61B 17/70; A61B 17/80; A61B 17/86

[52] U.S. Cl. .................. 606/61; 606/69; 606/73; 403/3; 403/384

[58] Field of Search .................. 606/61, 60, 69, 606/70, 71, 73; 403/3, 384, 388, 362, 199, 192, 398, 400

[56] References Cited

U.S. PATENT DOCUMENTS

| | | | |
|---|---|---|---|
| 4,773,402 | 9/1988 | Asher et al. | 606/61 |
| 5,171,279 | 12/1992 | Mathews | 606/61 |
| 5,257,994 | 11/1993 | Lin | 606/61 |
| 5,342,361 | 8/1994 | Yuan et al. | 606/61 |
| 5,344,422 | 9/1994 | Frigg | 606/61 |
| 5,374,267 | 12/1994 | Siegal | 606/61 |

Primary Examiner—Stephen C. Pellegrino
Assistant Examiner—Scott B. Markow
Attorney, Agent, or Firm—Tarolli, Sundheim & Covell

[57] ABSTRACT

An apparatus for interconnecting a pair of longitudinal members connectable with vertebrae of a spinal column comprises first and second connector members connectable with the longitudinal members and a rod extendable transverse to the longitudinal members and between the first and second connector members. The first connector member includes a recess for receiving the rod and a set screw for clamping the rod in the recess. The first connector member includes an opening through which a fastener for connecting one of the longitudinal members to the spinal column is extendable.

19 Claims, 4 Drawing Sheets

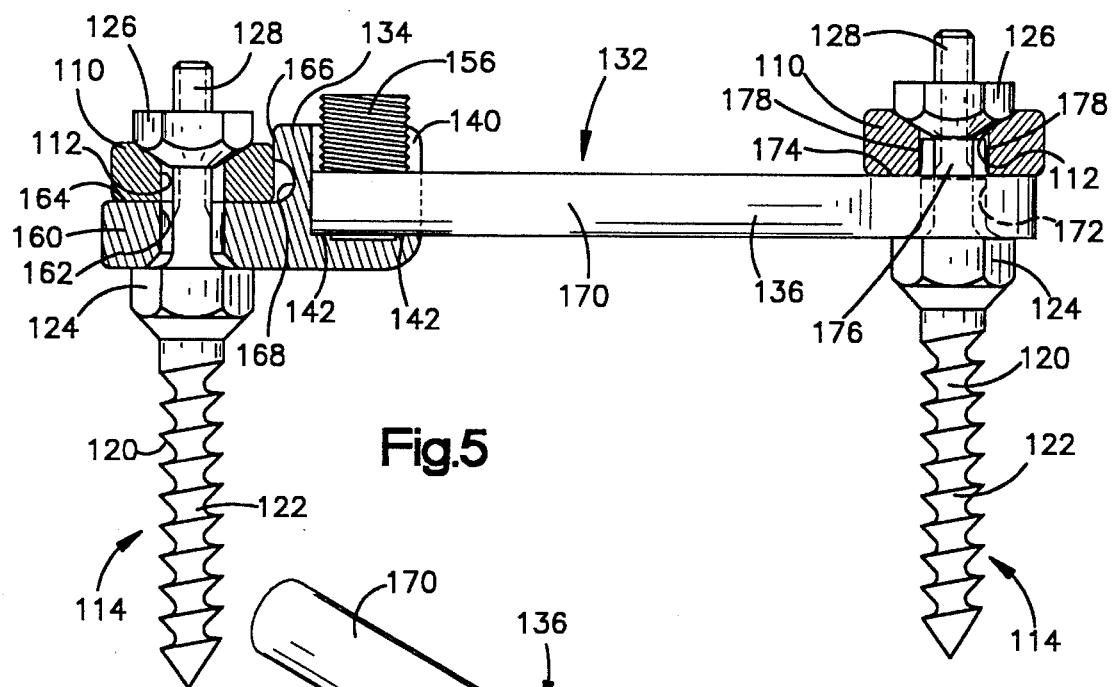
Fig.5
Fig.6
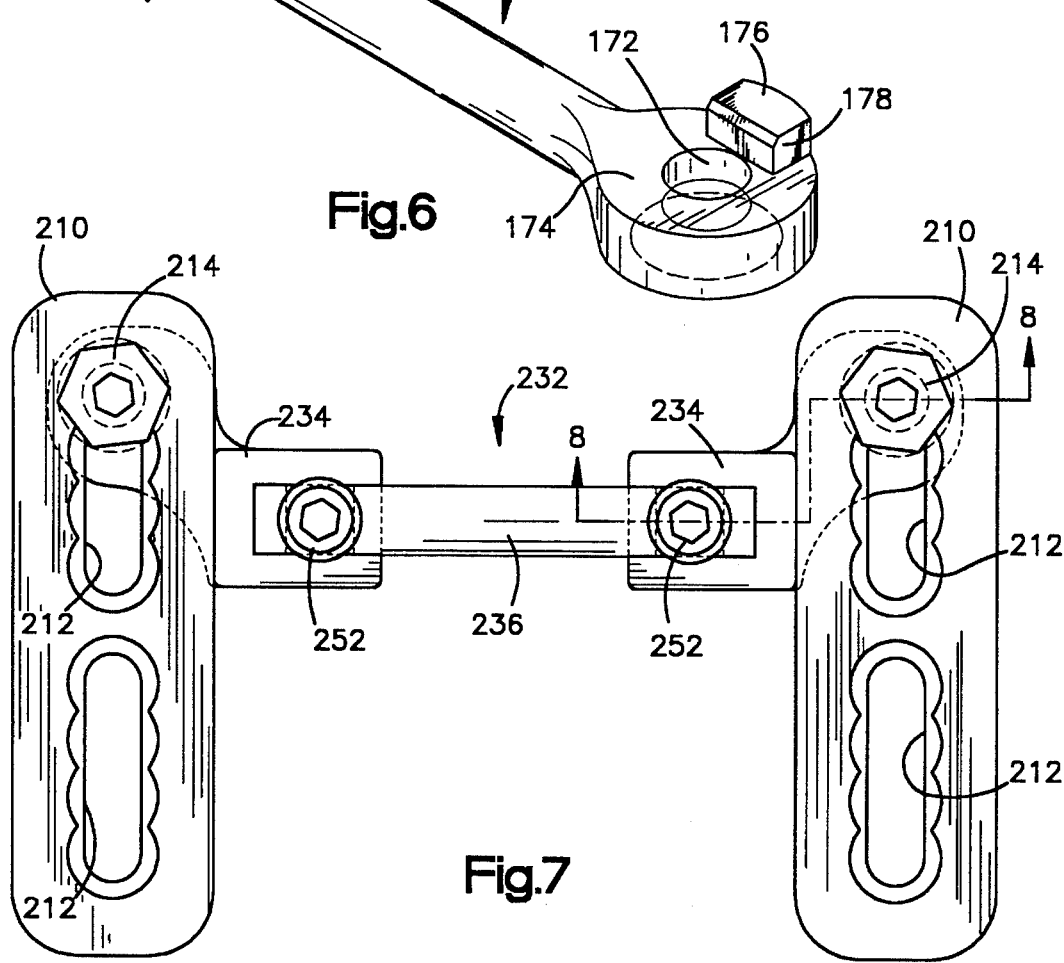
Fig.7

TRANSVERSE CONNECTOR FOR SPINAL COLUMN CORRECTIVE DEVICES

BACKGROUND OF THE INVENTION

The present invention relates to transverse connectors for interconnecting longitudinal members of a spinal column corrective device.

Transverse connectors for interconnecting longitudinal members of a spinal column corrective device are known. U.S. Pat. No. 5,084,049 discloses a pair of longitudinal members which are connectable with vertebrae of a spinal column. In one embodiment, an elongate plate with elongate openings extends transverse to longitudinal members. First and second attaching means connect the elongate plate with the longitudinal members. The first and second attaching means are movable along the length of the elongate openings in the elongate plate to change the location in which the first and second attaching means attaches the elongate plate to the longitudinal members.

In other embodiments, an elongate rod having threaded axial end portions extends transverse to the longitudinal members. Each of the end portions of the elongate rod are attached to the longitudinal members by clamps. Each of the clamps comprises first and second portions to apply a clamping force to a portion of the longitudinal member.

Each of the prior art embodiments are somewhat difficult to use and may interfere with surrounding tissue. The elongate plate used to interconnect longitudinal members extends laterally beyond the longitudinal members. The elongate rod and clamps may also extend laterally beyond the longitudinal members that are being interconnected and extend posteriorly of the longitudinal members.

SUMMARY OF THE INVENTION

The present invention is directed to a transverse connector for interconnecting a pair of longitudinal members, such as spine plates, which are connectable with vertebrae of a spinal column. In some embodiments of the present invention, the transverse connector comprises first and second connector members connectable with the longitudinal members. A rod extends transverse to the longitudinal members and interconnects the first and second connector members. The first connector member includes a recess for receiving the rod and means for clamping the rod in the recess.

Fasteners for connecting spine plates to the vertebrae are extendable through the first and second connector members to connect the connector members to the spine plates. The second connector member may include a recess for receiving the rod and means for clamping the rod in the recess in the second connector member. In one embodiment, the rod is integrally formed with the second connector member. In yet another embodiment, the means for clamping the rod in the first and second connector members are spaced a distance measured along the longitudinal axes of the spine plates from the openings in the first and second connector members through which the fasteners extend.

In all embodiments of the present invention, the transverse connectors have a low profile. That is, the transverse connectors do not extend posteriorly from the longitudinal members a substantial distance. Furthermore, the rods extending between the first and second connector members do not extend laterally beyond the longitudinal members.

BRIEF DESCRIPTION OF THE DRAWINGS

Further features of the present invention will become apparent to those skilled in the art to which the present invention relates from reading the following specification with reference to the accompanying drawings, in which:

FIG. 5 is an enlarged cross-sectional view of the transverse connector in FIG. 4, taken approximately along the line 5—5 in FIG. 4;

FIG. 6 is an enlarged pictorial view of a connector member in FIG. 5;

FIG. 7 is a plan view similar to FIGS. 1 and 4 illustrating yet another embodiment of the present invention;

DESCRIPTION OF PREFERRED EMBODIMENT

Figure 1:
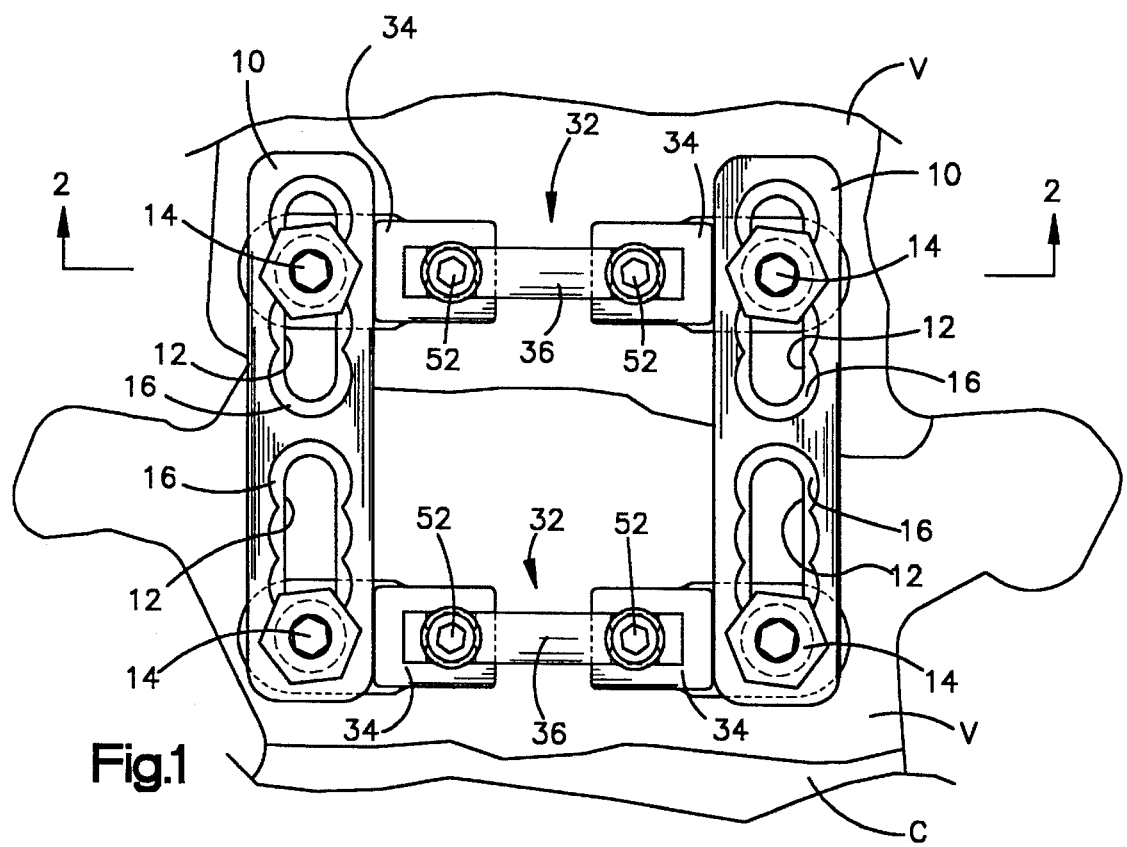
FIG. 1 is an enlarged plan view of one embodiment of the transverse connector of the present invention interconnecting a pair of spine plates which are connected to a spinal column.
Figure 2:
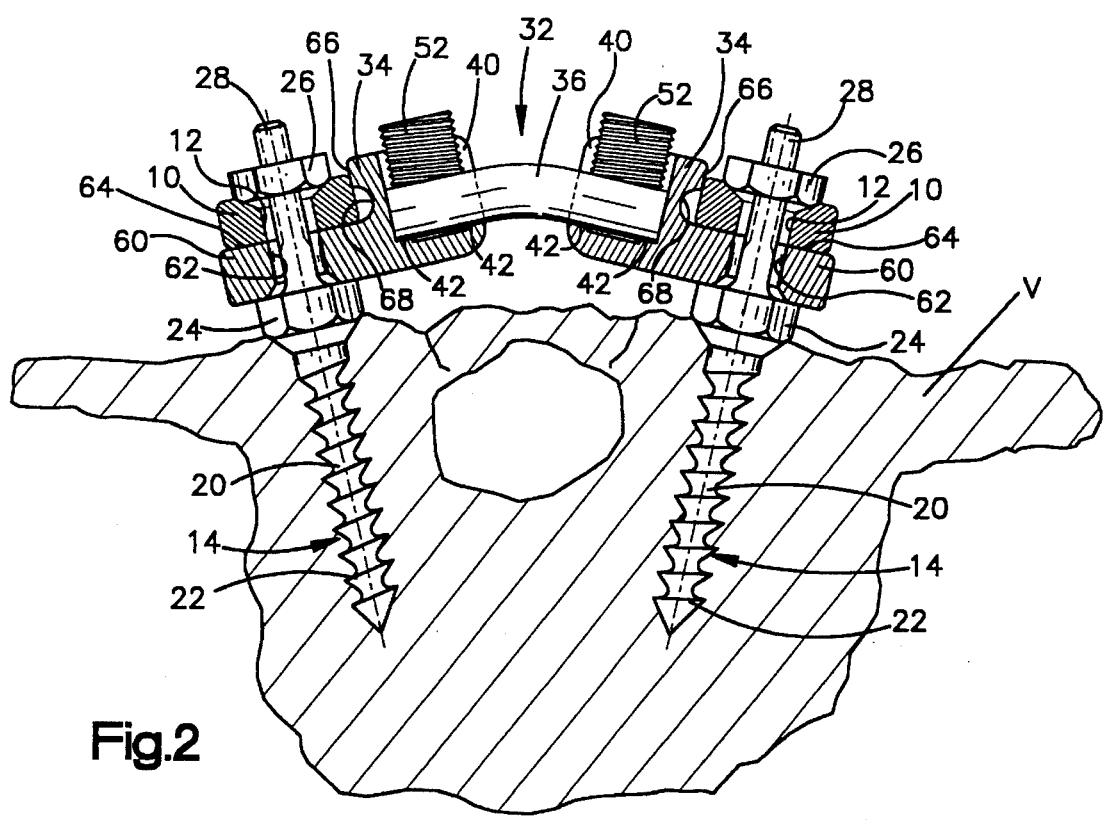
FIG. 2 is an enlarged cross-sectional view of the transverse connector in FIG. 1 interconnecting the spine plates, taken approximately along the line 2—2 in FIG. 1.
Figure 3:
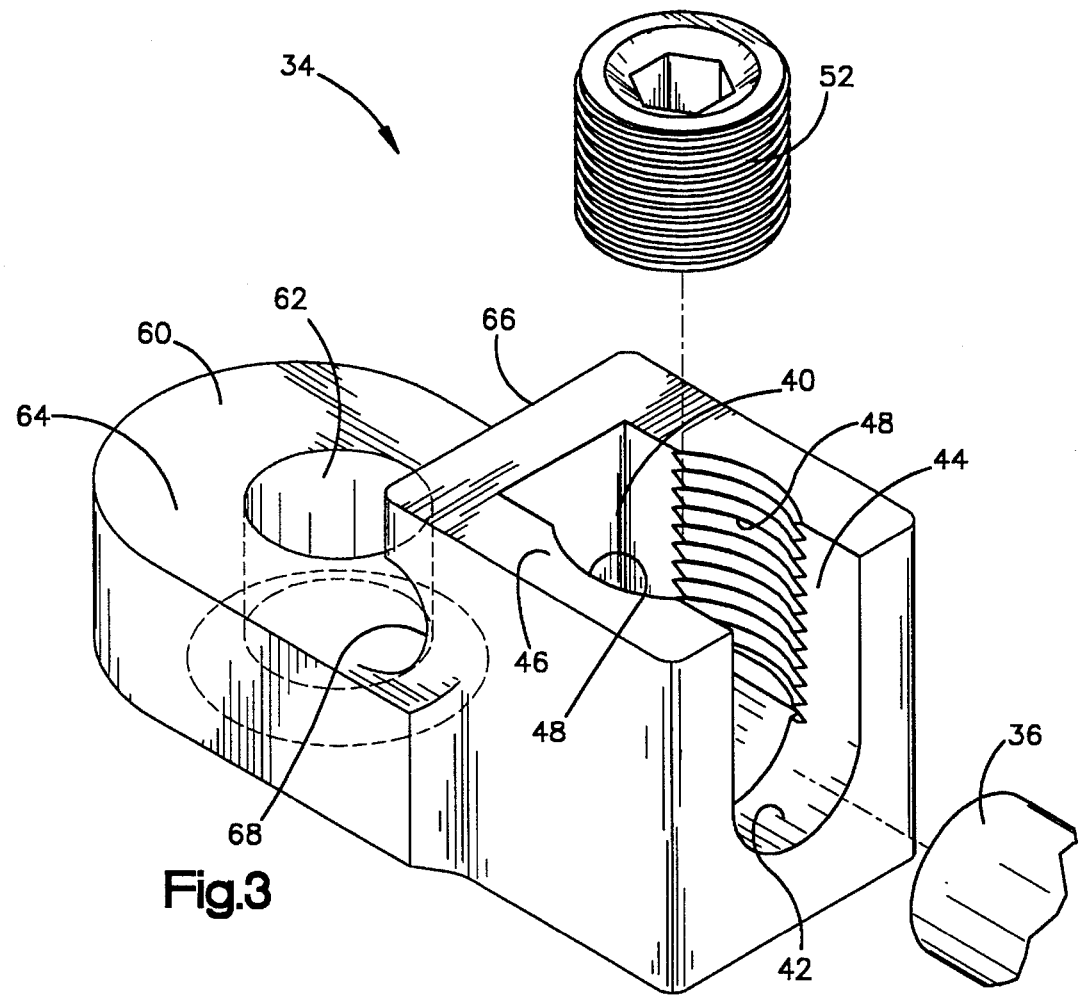
FIG. 3 is an enlarged pictorial view of a connector member in FIG. 1.

One embodiment of the present invention is illustrated in FIGS. 1–3. A portion of a spinal column C (FIG. 1) includes a plurality of vertebrae V. A pair of spine plates 10 are connected to some of the vertebrae V to maintain the relative positions of the vertebrae. It will be apparent that the spine plates 10 may be located anywhere along the spinal column C. The spine plates 10 of FIG. 1 are illustrated as being connected to two vertebrae V for example purposes only and it is apparent that the spine plates 10 could be any length and extend over any number of vertebrae V.

Each of the spine plates 10 is elongate and has a sufficient length to span several vertebrae V. A plurality of elongate openings 12 extend through each spine plate 10. The openings 12 receive fasteners 14, as illustrated in FIG. 2, to connect each of the spine plates to a vertebra V. A plurality of frustoconical-shaped recesses 16 are spaced along the length of each opening 12 which receive the fasteners 14.

Each fastener 14 includes a bone screw 20 (FIG. 2) having a threaded portion 22 threaded into a cancellous portion of the vertebra V. A shoulder 24 on the screw 20 spaces the spine plate 10 away from the vertebra V. The fastener 14 also includes a nut 26 which is threaded onto an outer threaded portion 28 of the screw 20 which extends through the opening 12 in the plate 10. The nut 28 is received in one of the recesses 16 spaced along the opening 12. The nut 26 clamps the plate 10 to the screw 20.

A pair of transverse connectors 32 (FIG. 1) interconnect the spine plates 10. The transverse connectors 32 block relative movement of the spine plates 10 so the vertebrae V connected to the spine plates are maintained in their desired relative positions and do not pivot relative to the anterior/posterior axis or a longitudinal central axis of the spinal column C. The transverse connectors 32 are located near axially opposite end portions of the spine plates 10 so the resulting structure forms a parallelogram. Although a pair of transverse connectors 32 are shown interconnecting the spine plates 10, it is apparent that any number of transverse connectors could be used to interconnect the plates.

Each transverse connector 32 (FIGS. 1 and 2) includes a pair of identical connector members 34. A rod 36 extends transverse to the spine plates 10 and interconnects the connector members 34. Each of the connector members 34 includes a recess 40 (FIG. 3) for receiving the rod 36. The recess 40 includes a pair of axially spaced arcuate surfaces 42 which project into the recess. The pair of axially spaced arcuate surfaces 42 engage portions of the rod 36 at axially spaced locations. Reference is hereby made to U.S. Pat. No. 5,024,213 to Asher et al. and assigned to the same assignee as the present invention. U.S. Pat. No. 5,024,213 describes the arcuate surfaces and their function in greater detail.

An opening 44 in a side surface 46, spaced posteriorly from the arcuate surfaces 42, allows the rod 36 to be dropped into the recess 40. Sidewalls 48 of the recess 40 are threaded for threadably receiving a set screw 52 for clamping the rod 36 against the arcuate surfaces 42.

Each of the connector members 34 (FIGS. 2 and 3) includes a mounting portion 60 having an opening 62 through which the outer threaded portion 28 of the screw 20 is extendable. The mounting portion 60 includes a side surface 64 against which the plate 10 is clamped by the nut 26. The plate 10 and connector member 34 are clamped together between the nut 26 and the shoulder 24 of the screw 20, as seen in FIG. 2. The connector member 34 includes a side surface 66 for engaging a side surface of the plate 10 to prevent relative pivoting between the connector member 34 and the plate 10. A concave surface 68 extends from the surface 66 to the surface 64 of the mounting portion 60.

The rod 36 can be cut to any length depending on the distance between the plates 10. The rod 36 can also be bent to conform to any desired shape, as seen in FIG. 2. The longitudinal axis of the rod 36 extends closer to the vertebra V than the longitudinal axes of the plates 10. The longitudinal axes of the plates 10 are located posteriorly to the longitudinal axis of the rod 36 to provide a low profile transverse connector 32.

Figure 4:
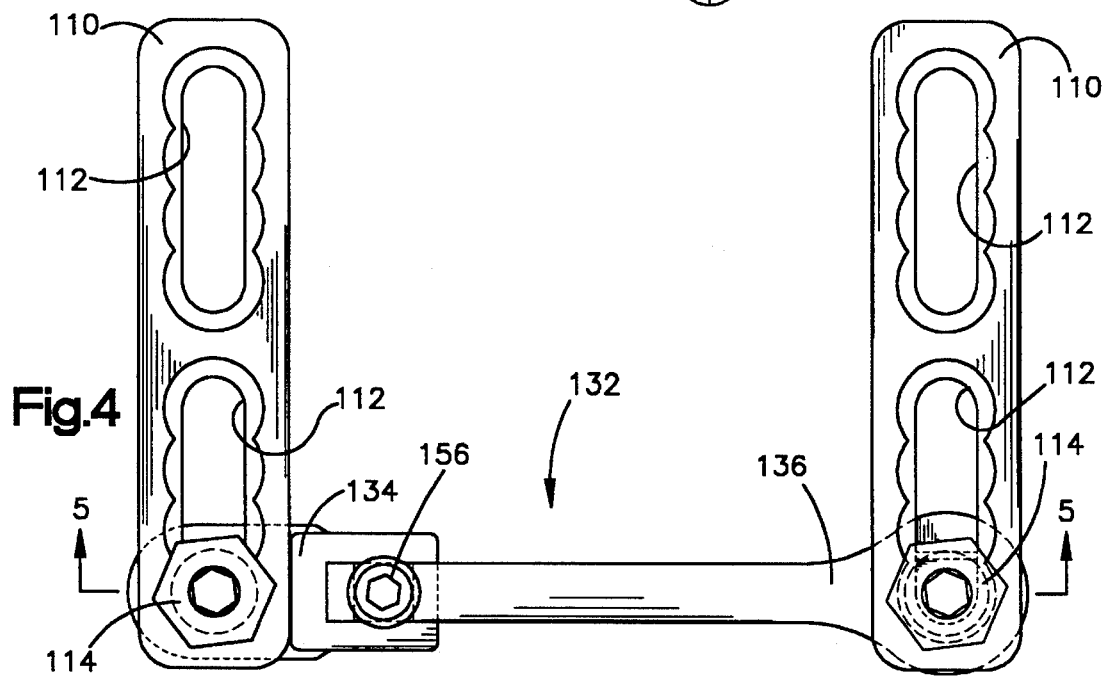
FIGS. 4 is a plan view similar to FIG. 1 illustrating another embodiment of the transverse connector of the present invention.

Another embodiment of the transverse connector of the present invention is illustrated in FIGS. 4–6. Spine plates 110 are connected to vertebrae (not shown) of a spinal column. Each spine plate 110 has a plurality of elongate openings 112 which receive fasteners 114 to connect the spine plates to the vertebrae, as described in connection with the embodiment of FIGS. 1 and 2. Each fastener 114 is identical to the fastener 14 described in connection with the embodiment of FIGS. 1 and 2. Each fastener 114 (FIG. 5) includes a bone screw 120 having a threaded portion 122 for engaging a vertebra, a shoulder 124 and a nut 126 threaded onto an outer threaded portion 128 which extends through the opening 112.

At least one transverse connector 132 (FIG. 4) interconnects the spine plates 110 to block relative movement between the spine plates 110 so the vertebrae connected to the spine plates are maintained in their desired relative positions. The transverse connector 132 includes connector members 134 and 136. The connector member 134 is identical to the connector members 34 of the embodiment of FIGS. 1–3 and therefore, will not be described in detail.

The connector member 134 (FIG. 5) includes a recess 140 for receiving a rod portion 170 of the connector member 136 extending transverse to the plates 110. A set screw 152 clamps the rod portion 170 against axially spaced arcuate surfaces 142 in the recess 140. The outer threaded portion 128 of the screw 120 extends through an opening 162 in a mounting portion 160 of the connector member 134. The nut 126 clamps the plate 110 against a surface 164 of the connector member 134 and to the shoulder 124 of the screw 120. The connector member 134 includes a side surface 166 for engaging a side surface of the plate 110. A concave surface 168 extends from the side surface 166 to the surface 164.

The connector member 136 (FIGS. 5 and 6) includes a rod portion 170 which is received in the recess 140 in the connector member 134. The end portion 128 of the screw 120 extends through an opening 172 in the connector member 136. The nut 126 clamps the plate 110 against a surface 174 of the connector member 136 and to the shoulder 124 of the screw 120. A protrusion 176 of the connector member 136 extends into the elongate opening 112 in the plate 110. The protrusion 176 includes side surfaces 178 for engaging side surfaces defining the opening 112 in the plate 110. The protrusion 176 prevents pivoting between the plate 110 and the connector member 136.

The rod portion 170 of the connector member 136 can be cut to any length depending on the desired spacing between the plates 110. The rod portion 170 can be bent to any configuration to prevent the transverse connector 132 from engaging the vertebra. The longitudinal axis of the rod portion 170 extends closer to the vertebra than the longitudinal axes of the plates 110. The axes of the plates 110 are located posteriorly to the axis of the rod portion 170.

Figure 8:
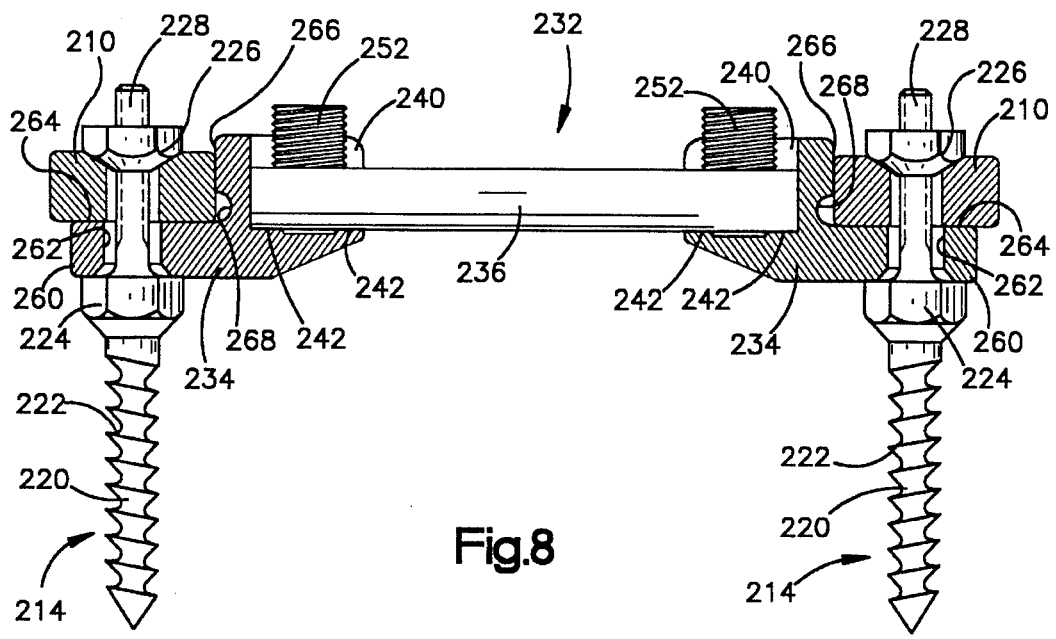
FIG. 8 is an enlarged cross-sectional view of the transverse connector in FIG. 7, taken approximately along the line 8—8 in FIG. 7.
Figure 9:
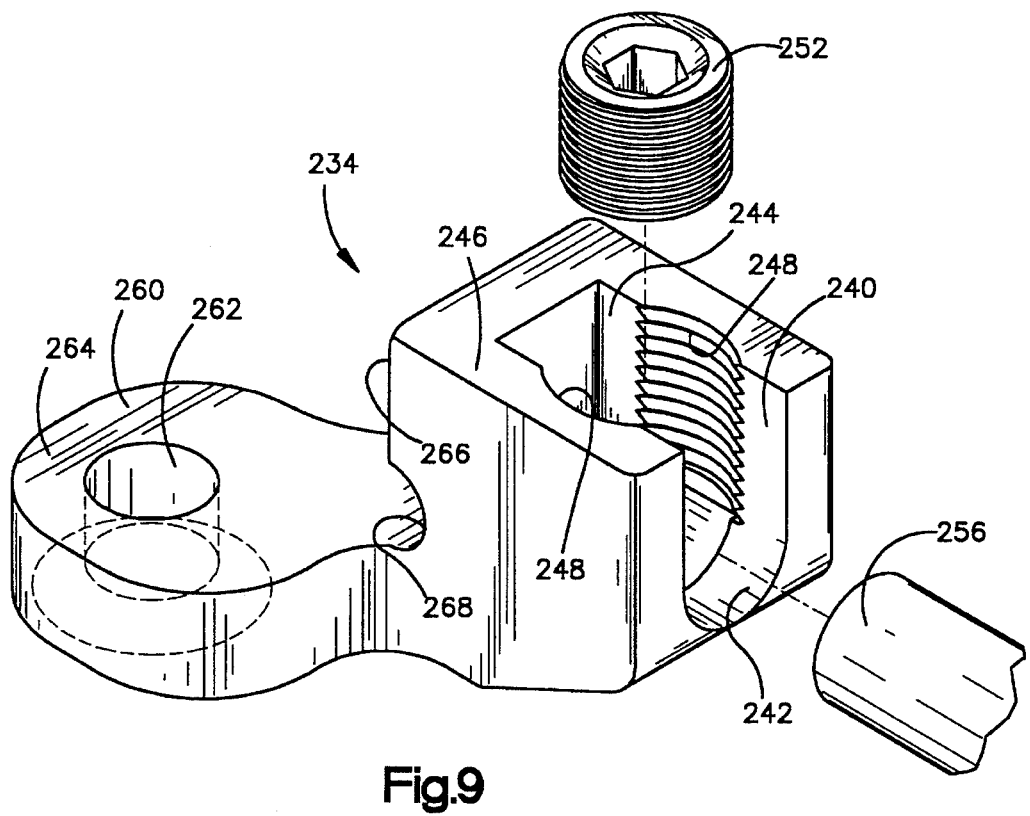
FIG. 9 is an enlarged pictorial view of a connector member in FIG. 7.

Another embodiment of the transverse connector of the present invention is illustrated in FIGS. 7–9. Spine plates 210 are connected to vertebrae (not shown) of a spinal column. Each spine plate 210 has a plurality of elongate openings 212 which receive fasteners 214 to connect the spine plates to the vertebrae, as described in connection with the embodiment of FIGS. 1 and 2. Each of the fasteners 214 is identical to the fasteners 14 described in connection with the embodiment of FIGS. 1 and 2. Each of the fasteners 214 (FIG. 8) includes a bone screw 220 having a threaded portion 222 engaging a vertebra, a shoulder portion 224, and a nut 226 which is threaded onto an outer threaded portion 228 which extends through an opening 212.

At least one transverse connector 232 (FIGS. 7 and 8) interconnects the spine plates 210. The transverse connector 232 blocks relative movement between the spine plates 210 so the vertebrae connected to the spine plates are maintained in their desired relative positions. The transverse connector 232 includes a pair of connector members 234 and a rod 236 extending transverse to the spine plates 210 and interconnecting the connector members. The connector members 234 are mirror images of each other.

Each of the connector members 234 (FIGS. 8 and 9) includes a recess 240 for receiving the rod 236. Axially spaced arcuate surfaces 242 in the recess 240 engage the rod 236 at axially spaced locations. The rod 236 is movable through an opening 244 (FIG. 9) in a posteriorly facing side surface 246 of the connector member 234. Sidewalls 248 defining the recess 240 are threaded for receiving a set screw 252 to clamp the rod 236 against the arcuate surfaces 242.

The connector member 234 (FIGS. 8 and 9) includes a mounting portion 260 with an opening 262 through which the outer threaded portion 228 of the screw 220 extends. The opening 262 is spaced from the set screw 252 a distance measured along the longitudinal axis of the plate 210 when the transverse connector 232 interconnects the spine plates, as seen in FIG. 7.

The nut 226 (FIG. 8) clamps the spine plate 210 against a surface 264 of the mounting portion 260 and to the shoulder 224 of the screw 220. The connector member 234 includes a side surface 266 which engages a side surface of the spine plate 210 to prevent pivoting of the spine plate relative to the connector member. A concave surface 268 extends from the side surface 266 to the surface 264 of the mounting portion 260.

The rod 236 can be cut to any length depending on the desired spacing between the plates 210. The rod 236 can be bent to any configuration to prevent the transverse connector 232 from engaging the vertebra. The longitudinal axis of the rod 236 extends closer to the vertebra than the longitudinal axes of the plates 210. The axes of the plates 210 are located posteriorly to the axis of the rod 236 to provide a low profile transverse connector 232.

As is apparent from the description of the transverse connectors, the connector members from the various embodiments may be used in conjunction with each other.

From the above description of the invention, those skilled in the art will perceive improvements, changes and modifications. Such improvements, changes and modifications within the skill of the art are intended to be covered by the appended claims.

Having described the invention, the following is claimed:

1. An apparatus for interconnecting a pair of longitudinal members extending substantially parallel to each other and connected with vertebrae of a spinal column by a plurality of fasteners for retaining vertebrae in a desired spatial relationship, said apparatus comprising:

a first connector member connectable with one longitudinal member;

a second connector member connectable with the other longitudinal member; and a rod extendable transverse to the longitudinal members and extending between said first and second connector members to interconnect said first and second connector members;

said first connector member including a recess for receiving said rod, means for clamping said rod in said recess, said means for clamping said rod in said recess engaging said rod to press said rod into said recess, an opening through which one of the fasteners for connecting the one longitudinal member to the spinal column is extendable, the opening being spaced from said clamping means, and means for cooperating with the fastener to connect said first connector member with the one longitudinal member.

2. An apparatus as set forth in claim 1 wherein said second connector member includes a recess for receiving said rod and means for clamping said rod in said recess in said second connector member.

3. An apparatus as set forth in claim 1 wherein said rod is integrally formed with said second connector member.

4. An apparatus as set forth in claim 1 wherein the opening in said first connector member through which the fastener is extendable is spaced from said means for clamping said rod in said recess a distance measured transverse to a longitudinal axis of said rod.

5. An apparatus as set forth in claim 4 wherein said second connector member includes an opening through which a fastener for connecting the other longitudinal member to the spinal column is extendable.

6. An apparatus as set forth in claim 5 wherein said second connector member includes a recess for receiving said rod and means for clamping said rod in said recess, said means for clamping said rod in said recess in said second connector member engaging said rod to press said rod into said recess, the opening in said second connector member through which the fastener is extendable is spaced from said means for clamping said rod in said recess in said second connector member a distance measured transverse to a longitudinal axis of said rod.

7. An apparatus as set forth in claim 1 wherein one of said first and second connector members includes a retaining portion extendable into an opening in its respective longitudinal member to prevent relative rotation between said one of said first and second connector members and its respective longitudinal member.

8. An apparatus as set forth in claim 1 wherein said recess for receiving said rod is defined by an arcuate surface against which said rod is pressed by said clamping means, said first connector member having a first side surface for facing away from said arcuate surface and the vertebra when said first connector member is connected to the one longitudinal member, said first side surface having an opening through which said rod is movable to position said rod in said recess.

9. An apparatus as set forth in claim 1 further including means for spacing a longitudinal axis of said rod from the vertebra a first distance, and means for spacing longitudinal axes of the longitudinal members from the vertebra a second distance which is at least equal to said first distance when said apparatus interconnects the longitudinal members.

10. An apparatus as set forth in claim 1 wherein said first connector member includes surface means engageable with a side surface of the one longitudinal member to prevent pivoting between said first connector member and the one longitudinal member.

11. An apparatus for retaining vertebrae of a spinal column in a desired spatial relationship, said apparatus comprising:

first and second fasteners, each of said fasteners having a first end portion engageable with a vertebra, a second end portion, and an intermediate portion located between said first and second end portions;

first and second spine plates extendable substantially parallel to each other along the spinal column, said first spine plate including an opening through which said second end portion of said first fastener extends, said second spine plate including an opening through which said second end portion of said second fastener extends;

a rod extending transverse to said first and second plates and between said first and second plates;

a first connector member connected to said first plate and to said rod, said first connector member including an opening through which said second end portion of said first fastener extends, a recess into which said rod extends, and means for clamping said rod in said recess; and a second connector member connected to said second plate and to said rod, said second connector member including an opening through which said second end portion of said second fastener extends.

12. An apparatus as set forth in claim 11 further including a nut threadably engaging said second end portion of said first fastener, said first plate and said first connector member being clamped between said nut and said intermediate portion of said first fastener.

13. An apparatus as set forth in claim 12 wherein said nut includes surface means for engaging said first plate and said first connector member includes surface means for engaging said intermediate portion of said first fastener.

14. An apparatus as set forth in claim 11 wherein said rod is integrally formed with said second connector member.

15. An apparatus as set forth in claim 14 wherein said second connector member includes a retaining portion extending into the opening in said second plate, said retaining portion including surface means for engaging surfaces defining the opening in said second plate to prevent pivoting of said second connector member relative to said second plate.

16. An apparatus as set forth in claim 11 wherein said first connector member includes a surface engaging a side surface of said first plate to prevent pivoting of said first connector member relative to said first plate.

17. An apparatus as set forth in claim 11 wherein said means for clamping said rod in said recess in said first connector member is spaced from the opening in said first connector member a distance measured along a longitudinal axis of said first plate.

18. An apparatus as set forth in claim 17 wherein said second connector member includes a recess into which said rod extends and means for clamping said rod in said recess in said second connector member, said means for clamping said rod in said recess in said second connector member being spaced from the opening in said second connector member a distance measured along a longitudinal axis of said second plate.

19. An apparatus as set forth in claim 11 wherein a longitudinal axis of said rod is spaced from each of said intermediate portions of said first and second fasteners a distance which is at most equal to the distance that longitudinal axes of said first and second plates are spaced from each of said intermediate portions of said first and second fasteners.

* * * * *